(12) United States Patent
Horndeski

(10) Patent No.: US 11,896,477 B2
(45) Date of Patent: Feb. 13, 2024

(54) APPARATUS, SYSTEM AND METHODS FOR IMPROVED BREAST SURGERY WITH MYOINTEGRATION

(71) Applicant: Gary Horndeski, League City, TX (US)

(72) Inventor: Gary Horndeski, League City, TX (US)

(73) Assignee: INNOVELLUM, LLC, Lake Forest, IL (US)

( * ) Notice: Subject to any disclaimer, the term of this patent is extended or adjusted under 35 U.S.C. 154(b) by 261 days.

(21) Appl. No.: 17/186,693

(22) Filed: Feb. 26, 2021

(65) Prior Publication Data

US 2021/0177571 A1     Jun. 17, 2021

Related U.S. Application Data

(63) Continuation of application No. 16/155,550, filed on Oct. 9, 2018, now Pat. No. 10,932,899.

(60) Provisional application No. 62/569,862, filed on Oct. 9, 2017.

(51) Int. Cl.
| | | |
|---|---|---|
| *A61F 2/12* | (2006.01) | |
| *A61F 2/00* | (2006.01) | |
| *B29L 31/00* | (2006.01) | |

(52) U.S. Cl.
CPC .............. *A61F 2/12* (2013.01); *A61F 2/0063* (2013.01); *A61F 2/0077* (2013.01); *A61F 2002/0086* (2013.01); *A61L 2430/04* (2013.01); *B29L 2031/7532* (2013.01)

(58) Field of Classification Search
CPC ........ A61F 2/12; A61F 2/0063; A61F 2/0077; A61F 2002/0086; A61L 2430/04; B29L 2031/7532
See application file for complete search history.

(56) References Cited

U.S. PATENT DOCUMENTS

| | | |
|---|---|---|
| 2,661,744 A | 12/1953 | Browner |
| 7,520,896 B2 | 4/2009 | Benslimane |
| 8,632,454 B2 * | 1/2014 | Lashinski .......... A61B 17/0401 606/151 |

(Continued)

OTHER PUBLICATIONS https://www.youtube.com/watch?v=Dfby4xWX4ak; AmerraMedical Mar. 20, 2015 (Year: 2015).

*Primary Examiner* — Suzette J Gherbi

(57) ABSTRACT

The present disclosure is directed to Myointegration, the improvement of breast implant apparatus, system and methods for a design that extends the breast implant centrifugally, or in which a separate device is utilized in combination with a breast implant, that has one or more straps originating from the breast implant extension or from the separate device. The one or more straps are looped through the pectoralis major muscle then back into the implant extension or the separate device repeatedly. The straps are eventually attached in some manner to themselves, to the implant extension, or to the separate device. Since the pectoralis major muscle contains neuromuscular spindles that sense length, velocity and acceleration, when the user changes position from supine to vertical, the gravitational force generated by the mass of the breast implant pulls on the strap or straps, which pulls the muscle and stimulates the neuromuscular spindles, thereby generating lift of the implanted breast insert.

8 Claims, 12 Drawing Sheets

(56) References Cited

U.S. PATENT DOCUMENTS

| | | | |
|---|---|---|---|
| 8,876,899 B2 | 11/2014 | Maxwell | |
| 9,220,589 B2 | 12/2015 | Lashinski | |
| 9,763,770 B2 * | 9/2017 | Lee | A61B 17/06166 |
| 10,039,857 B2 * | 8/2018 | Bishop | A61L 17/00 |
| 10,307,237 B2 * | 6/2019 | Wang | A61L 27/3666 |
| 10,568,728 B2 * | 2/2020 | Felix | A61L 27/50 |
| 2006/0167338 A1 * | 7/2006 | Shfaram | A61B 17/0487 |
| | | | 606/139 |
| 2008/0082129 A1 | 4/2008 | Jones | |
| 2010/0331612 A1 * | 12/2010 | Lashinski | A61B 17/0401 |
| | | | 600/37 |
| 2014/0046442 A1 * | 2/2014 | Guterman | A61B 17/84 |
| | | | 623/8 |
| 2015/0112434 A1 | 4/2015 | Felix | |
| 2015/0351899 A1 * | 12/2015 | Mortarino | A61F 2/12 |
| | | | 623/8 |
| 2016/0331504 A1 | 11/2016 | Wang | |
| 2017/0196672 A1 * | 7/2017 | Guterman | A61B 17/84 |
| 2017/0348090 A1 * | 12/2017 | Saint | A61F 2/0063 |
| 2018/0015152 A1 * | 1/2018 | Yang | A61K 31/7088 |
| 2018/0200044 A1 * | 7/2018 | Doucet | A61F 2/12 |
| 2018/0325512 A1 * | 11/2018 | Ruff | A61B 17/06166 |
| 2019/0142573 A1 * | 5/2019 | Mlodinow | A61F 2/12 |
| | | | 623/8 |
| 2019/0336273 A1 * | 11/2019 | Bertoli | A61F 2/12 |

\* cited by examiner

APPARATUS, SYSTEM AND METHODS FOR IMPROVED BREAST SURGERY WITH MYOINTEGRATION

The present application is a continuation of and claims priority to U.S. Non-Provisional patent application Ser. No. 16/155,550, filed Oct. 9, 2018, issued as U.S. Pat. No. 10,932,899 on Mar. 2, 2021, and entitled "APPARATUS, SYSTEM AND METHODS FOR IMPROVED BREAST SURGERY WITH MYOINTEGRATION" and U.S. Provisional Patent Application Ser. No. 62/569,862, filed Oct. 9, 2017, now expired, and entitled "APPARATUS, SYSTEM AND METHODS FOR IMPROVED BREAST SURGERY". The entirety of which are hereby incorporated by reference.

FIELD OF THE DISCLOSURE

The present disclosure relates to an apparatus, system and methods for improved breast surgery, including using the patient's muscles to generate lift of an implanted breast insert or of the breast itself. In particular, the present disclosure relates to an improvement in breast and breast implants, devices and surgery in which the pectoralis major muscle is used, in combination with the breast, breast implant, one or more straps and/or a separate device, to generate active lift by the patient. Additionally, the devices, systems and methods described herein can be utilized in other locations in the body with similar beneficial results.

The novelty of the present disclosure is a design that extends the breast implant centrifugally, or in which a separate device is utilized in combination with a breast implant, that has one or more straps originating from the breast implant extension or from the separate device. The one or more straps are looped through the pectoralis major muscle then back into the implant extension or the separate device repeatedly. The straps are eventually attached to themselves, to the implant extension, or to the separate device. Although there are many ways to attach the straps, they can be sewn, stapled, tied, or connected in other known ways. Since the pectoralis major muscle contains neuromuscular spindles that sense length, velocity and acceleration, when a woman changes position from supine to vertical, the gravitational force generated by the mass of the breast implant pulls on the strap or straps, which pulls the muscle and stimulates the neuromuscular spindles, thereby generating lift of the implanted breast insert.

The present disclosure relates to an apparatus, for example the separate device, with or without a strap or straps. The present disclosure also relates to a system that includes at a minimum, a breast implant, a separate device that is implanted along with the breast insert, and a strap or straps, all separate (or in various combinations), but used together to accomplish the novel results of the disclosure. As described in detail herein, the present disclosure may include the separate device along with the straps, or may use a breast implant configured to allow the straps to connect or attach to the breast implant without the need for a separate device. The present disclosure relates to the method or methods for improved breast implant surgery that includes utilizing the apparatus and/or system, as described in detail herein, and which take advantage of the novelty and benefits of the present disclosure.

BACKGROUND OF THE DISCLOSURE

Women desire beautiful breasts that are functional, pain free and without foreign material. Vertical scars, insufficient elevation, inadequate upper pole fullness, nipple numbness and loss of breast-feeding are undesirable. Further, relieving pain attributed to enlarged breasts has required significant tissue removal.

Breast beauty is determined by culture and requires harmony between the breast and the body. In the eye of the beholder, beauty creates a perception of pleasure and generates attraction. In women, it creates psychological well-being.

The fashion industry capitalizes on beauty and contributes to the cultural standards. A female mannequin may represent fashion's ideal breasts, in which the breasts are large, symmetrical hemispheres that begin at the horizontal axillary line but do not extend lateral to the anterior axillary line. The combination of large hemispheres within these horizontal and vertical constraints creates upper pole fullness, anterior projection, cleavage and a high inframammary folds.

Plastic surgeons also capitalize on beauty and contribute to cultural standards. The most frequently performed aesthetic operation is breast augmentation, which creates large hemispherical breasts similar to the mannequin. Mastopexies and reductions are not as popular as breast augmentations and do not achieve mannequin like results. The breasts have vertical scars, insufficient elevation, inadequate upper pole fullness, minimal projection and poor cleavage. The inframammary fold remains low and the breast extends lateral to the anterior axillary line. Nipple numbness and loss of breast-feeding are frequent complications.

In practice, the goal of mastopexies is to transpose the breast to an aesthetically desired position and maintain it. Multiple techniques using the external skin envelope have been described. Unfortunately, as the dermis ages, the decreased elasticity requires greater stretch to generate the passive force needed to oppose gravity. Progressive stretching results in recurrent breast descent. Other alternatives are passive internal suspensions using dermis or synthetic materials. These mastopexies are limited by the material providing the support and their points of attachment. Dynamic forces can exceed the mechanical strength at the points of attachment, resulting in failure and descent.

Accordingly, one of the problems is that breast implants are continuously exposed to gravity, resulting in descent and shape change. Attempts to prevent descent have included Dacron patches, tabs, textured surfaces, or implantpexy with biological or synthetic materials. All of these techniques use passive force to oppose gravity.

Various patents and patent applications have attempted to address the disadvantages of breast surgeries, breast implants and various devices described herein. One example that pertains to anchors is U.S. Pat. No. 9,220,589, titled Minimally Invasive Breast Lift Method with a Superior Tissue Support and an Inferior Anchor, which discloses methods and an apparatus for use in supporting tissue in a patient's body. In certain disclosed embodiments, the patient's breast or another tissue is supported. One disclosed method involves introducing a superior soft tissue anchor into a patient, the anchor having an inferiorly facing total surface area. The same method also discloses introducing one or more inferior soft tissue anchors into the patient, such that the inferior soft tissue anchors are suspended from the superior soft tissue anchor, and the sum of all of the inferior soft tissue anchors has a superiorly facing total surface area. This inferiorly facing total surface area of the superior anchor can be greater, such as at least two times greater than the superiorly facing total surface area of the inferior anchors.

Another patent that pertains to an envelope, U.S. Pat. No. 7,520,896, titled Breast Implant, Use of an Associated Pouch, and Method for Determination of a Breast Implant, discloses a breast implant tailor-made for a patient comprising an envelope, which is made in particular of silicone elastomer and inside which a filler product is arranged, and also a securing element disposed on the envelope and intended to be connected to a support element. The support element is fixed substantially in the area of the axilla, or on the greater pectoral muscle of the patient.

Another example, a patent application pertaining to sutures is US Patent Publication No. US20080082129A1, titled Minimally-Invasive Mastoplasty Procedure and Apparatus, which discloses medical devices and methods for a minimally-invasive mastoplasty procedure, in which barbed sutures are used to accomplish the mastoplasty through puncture wounds by deploying the sutures caudally from stable anatomical features into the breast tissue.

Another patent pertaining to a biological interface, U.S. Pat. No. 8,876,899, titled Breast Implant Assembly, discloses a medical implant assembly and method having a medical implant, e.g. a breast prostheses, attached to a biological interface. The biological interface is comprised of a dermal material with capsular contracture inhibiting properties so that once the medical assembly is inserted into the host, the biological interface, which is intimately coupled to the implant, prevents or reduces capsular contracture formation around the implant. The biological interface comprises a plurality of apertures along its periphery, and attaches to the medical implant by receiving a plurality of attachment flaps or appendages located on the exterior surface of the medical implant within or through the apertures. The attachment of the biological interface is such that the assembly remains intact even where the attachment flaps loosen upon expansion of the implant after insertion into a host, as where the implant is therein injected to a desired dimension.

Another patent application pertaining to absorbable breast implants is US Patent Publication No. US20150112434A1, titled Absorbable Implants fir Plastic Surgery, which discloses the development of absorbable implants for breast surgery that conform to the breast parenchyma and surrounding chest wall. The implants support newly lifted breast parenchyma, and/or a breast implant. The implants have mechanical properties sufficient to support a reconstructed breast, and allow the in-growth of tissue into the implant as it degrades. The implants have a strength retention profile allowing the support of the breast to be transitioned from the implant to regenerated host tissue, without significant loss of support. Three-dimensional implants fir use in minimally invasive mastopexy/breast reconstruction procedures are also described, that confer shape to a patient's breast. These implants are self-reinforced, can be temporarily deformed, implanted in a suitably dissected tissue plane, and resume their preformed three-dimensional shape. The implants are preferably made from poly-4-hydroxy butyrate (P4HB) and copolymers thereof. The implants have suture pullout strengths that can resist the mechanical loads exerted on the reconstructed breast.

Yet another patent application pertaining to wrapping a composition around an implant is US Patent Publication No, US20160331504A1, titled Tissue Matrices and Methods of Treatment, which discloses methods, systems, and compositions for treatment. The methods can be used to stretch and completely or nearly completely wrap a composition around an implant or tissue expander. The systems can be used to protect an implant or tissue expander by completely or nearly completely wrapping a composition around the implant or tissue expander. The compositions can be used to completely or nearly completely wrap around an implant or tissue expander to provide support and protection to the implant or tissue expander.

None of these references successfully addresses the disadvantages and limitations of breast surgeries and devices used in those surgeries to the extent, and with the success, that the present disclosure encompasses. At a minimum, none of the references disclose that once the straps of the device are looped or threaded through the pectoral major muscle then back to the breast implant (configured for the straps) or back to the separate device, repeatedly, the straps are eventually attached to themselves, to the breast implant or to the separate device. Also, none of these references disclose that since the pectoralis major muscle contains neuromuscular spindles that sense length, velocity and acceleration, when the patient changes position from supine to vertical, the gravitational force generated by the mass of the breast implant pulls on the strap or straps, which in return pulls the muscle and stimulates the neuromuscular spindles to contract, thereby generating lift of the implanted breast insert. Further, none of the references disclose that the straps also compress the breast implant to maintain projection. As such, none of these references successfully addresses the shortcomings addressed by the present disclosure.

Accordingly, although breast implant methods currently exist, there is currently no apparatus, system or methods for an improved breast implant utilizing a device in combination with a breast implant and one or more straps, in which the straps are looped through the pectoralis major muscle then back into the implant extension or the device repeatedly, and in which the straps are eventually attached to themselves, to the breast implant or to the separate device, such that when a woman changes position from supine to vertical, the muscle automatically generates lift of the implanted breast insert. The present disclosure satisfies these needs.

SUMMARY OF THE DISCLOSURE

In general, and in order to solve the above-mentioned shortcomings in the field of breast implants, a new alternative is disclosed, called Myointegration, in which the patient's pectoralis major muscle is incorporated and used to generate active lift of the breast or breast implant. The configuration and art of this design extends the breast or breast implant centrifugally. Additionally, a separate device can be used in combination with a breast implant, in which one or more straps, originate from the implant extension or from the separate device.

Next, these straps are looped through the pectoralis major muscle then back into the implant extension or the separate device, repeatedly. Once completed, the straps are attached either to themselves, to the implant extension or to the separate device. There are many ways to attach the straps, such as sewing, stapling, or connecting in other known ways.

The pectoralis major muscle contains neuromuscular spindles that sense length, velocity and acceleration. When the patient changes position from supine to vertical, the gravitational force generated by the mass of the breast or breast implant pulls on the strap or straps, which pulls the muscle and stimulates the neuromuscular spindles.

Once stimulated, the pectoralis major muscle contracts, creating an active force pulling the implant (or the breast) back to original position. The straps are looped through the muscle end-to-side, which prevents overcorrection. The straps also compress the breast implant to maintain projection.

The laws of physics apply to biological systems including breasts and breast implants. The second law of thermodynamics describes the necessity of energy to maintain shape. For example, the breast implant is a soft open system that absorbs energy from earth's gravitational field resulting in shape change. The energy generated by the pectoral major muscle is transferred through the straps to maintain breast implant shape. The present disclosure maintains implant position by a negative feedback control system and opposes shape change by incorporating a new energy source.

Additionally, the system and methods described herein, in which one or more straps are looped through a muscle then back repeatedly, and eventually attached to themselves, can be utilized in other places in the body. Further, similar to the devices described herein for breast surgery, similar (although not necessarily identical) implant devices can be utilized for surgery in other locations in the body. Likewise, when a patient changes position, the gravitational force that is generated by will pull on the straps, which will then pull on the particular muscle and thereby stimulates the muscle to respond.

Additionally, combing computer-aided design with plastic surgical principals can create beautiful, functional breasts without foreign material. Vertical scars are avoided and weight transfer relieves pain. However, in some instances, artificial skin, such as synthetic material or biological material can be used with or instead of the patient's skin. By using synthetic material in these situations, the resulting breast may be an improvement over the resulting breast if the synthetic material were not available or used in the surgery.

Software analysis of chest images, physical measurements and desires are combined to generate a surgical blueprint. The breast is divided horizontally into two components preserving the neurovascular supply and major lactiferous ducts. The skin flap cephalad to the areola provides external coverage. The areola remains attached to a de-epithelized mound, which is rotated into a cone. Dermal straps originating from the base of the cone are looped through the pectoralis major muscle and the cone repeatedly.

As such, it is an object of the present disclosure to provide an improved breast implant apparatus, system and method that extends the breast implant centrifugally, or in which a separate device is utilized in combination with a breast implant, that has one or more straps originating from the breast implant extension (or the separate device).

It is also an object of the present disclosure to provide an improved breast implant apparatus, system and method in which a separate device is utilized in combination with a breast implant, that has one or more straps originating from the breast implant extension (or the separate device), with the one or more straps being looped through the pectoralis major muscle then back into the implant extension or the separate device repeatedly.

It is also an object of the present disclosure to provide an improved breast implant apparatus, system and method in which a separate device is utilized in combination with a breast implant, that has one or more straps originating from the breast implant extension (or the separate device), with the one or more straps being looped through the pectoralis major muscle then back into the implant extension or the separate device repeatedly, and eventually attached to themselves, to the implant extension, or to the separate device.

It is also an object of the present disclosure to provide an improved breast implant apparatus, system and method in which software analysis of the chest images, physical measurements and the woman's desires are combined to derive the optimal solution mathematically, using computer aided design modified to be applicable to breast surgery, for a technique that is universally applicable and generates individualized solutions that maximize results. Using the CAD system, a blueprint is developed for optimal placement of the one or more straps originating from the breast implant extension (or the separate device), with the one or more straps being looped through the pectoralis major muscle then back into the implant extension or the separate device repeatedly, and eventually attached to themselves, to the implant extension, or to the separate device, as set forth in the generated blueprint.

Additionally, it is an object of the present disclosure to provide an improved breast implant apparatus, system and method that present disclosure is a design that extends the breast implant centrifugally, or in which a separate device is utilized in combination with a breast implant, that has one or more straps originating from the breast implant extension (or the separate device), in which the one or more straps are looped through the pectoralis major muscle then back into the implant extension or the separate device repeatedly, and eventually attached to themselves, to the implant extension, or to the separate device, and since the pectoralis major muscle contains neuromuscular spindles that sense length, velocity and acceleration, when a patient changes position from supine to vertical, the gravitational force generated by the mass of the breast implant pulls on the strap or straps, which pulls the muscle and stimulates the neuromuscular spindles, thereby generating muscular lift of the implanted breast insert.

In a preferred embodiment the objective of the present disclosure is a design that extends the breast implant centrifugally, in which a device that has multiple straps originating from the device, in which the straps are looped through the pectoralis major muscle and then back into the device repeatedly, and eventually attached to the device. Since the pectoralis major muscle contains neuromuscular spindles that sense length, velocity and acceleration, when a patient changes position from supine to vertical, the gravitational force generated by the mass of the breast pulls on the straps, which pulls the muscle and stimulates the neuromuscular spindles, thereby generating muscular lift of the breast.

These and other aspects, features, and advantages of the present disclosure will become more readily apparent from the attached drawings and the detailed description of the preferred embodiments, which follow.

DRAWINGS

The preferred embodiments of the disclosure will be described in conjunction with the appended drawings provided to illustrate and not to the limit the disclosure, where like designations denote like elements, and in which.

DETAILED DESCRIPTION

Figure 1:
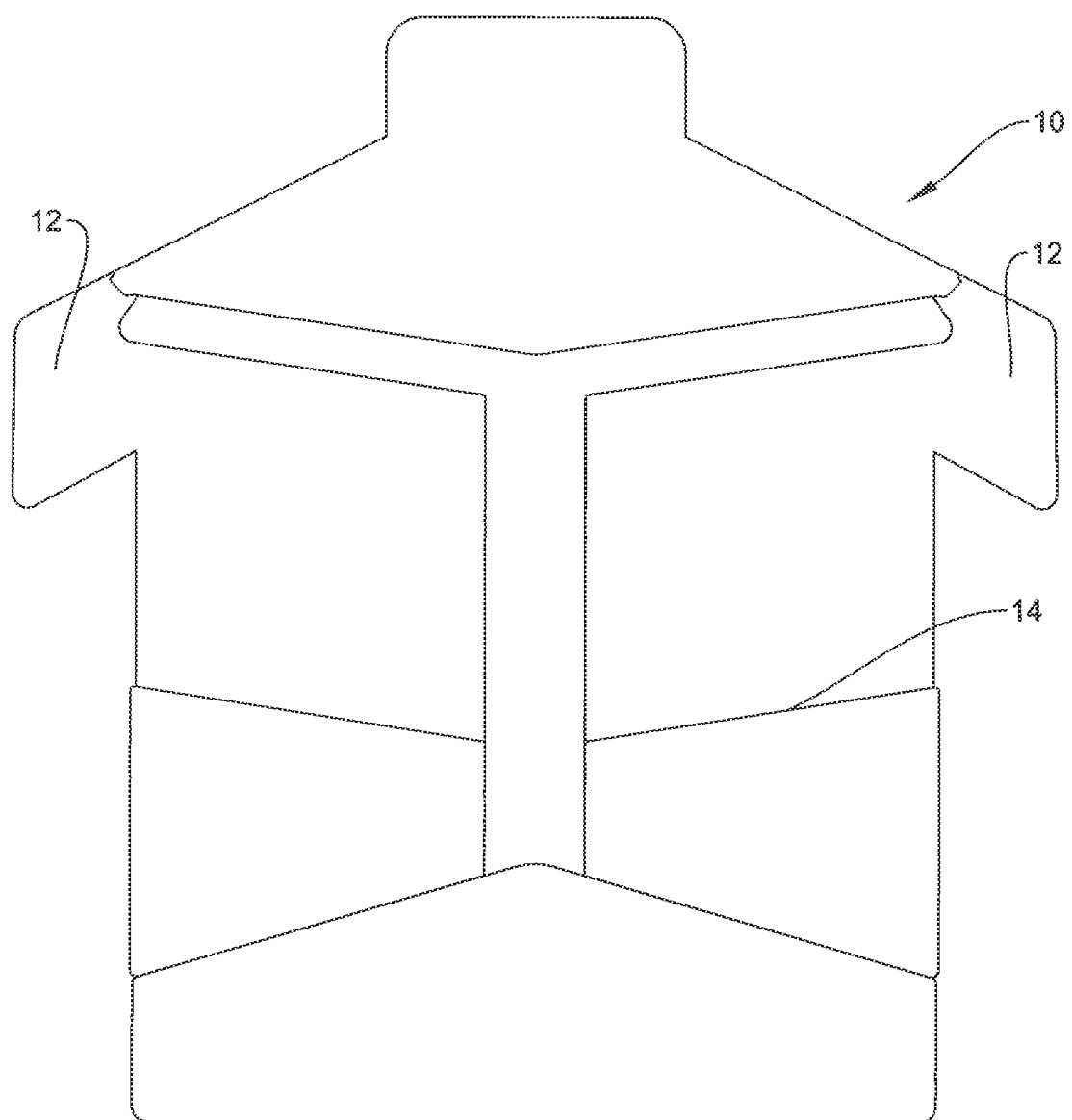
FIG. 1 illustrates an improved breast apparatus, system and method in accordance with one embodiment of the present disclosure.

Referring to the drawings, wherein like reference numerals refer to the same or similar features in the various views, the present disclosure pertains to an improved breast implant apparatus and system, and methods for improved breast implants, including utilizing a patient's muscles to react to the patient's movement and to generate lift of the implanted breast insert. In particular, the innovative and novel improvement in breast implants, devices and surgery utilize straps and the pectoralis major muscle, in combination with the breast implant and/or a separate device, to generate active lift by the patient's pectoralis major muscle.

This active force by the patient's muscle is an alternative to passive opposition. Since the breast lies superficial to the pectoral major muscle, which is capable of generating large forces along its axis, attaching a mechanical load perpendicular to the axis changes the muscle length. The neuromuscular spindles sense length, velocity, acceleration and the muscle compensates for changes. End-to-side weight transfer has the advantage of an active force and a negative feedback control system to maintain position. In-situ weight transfer preserves the muscle's original functions, responds to dynamic forces without mechanical failure or over correction, and provides lifetime active opposition to gravity.

Additionally, the muscle reshapes the breast tissue into a cone, transposes the cone cephalad-medial and compresses the cone to increase projection. The weight of the breast is transferred to the pectoralis major muscle, then onto the ribs, sternum, clavicle and humerus. This transfer of the weight decreases the external skin envelope pull on the neck, shoulder and upper back. Pain is relieved without significant weight removal. The weight transfer, apparatus, system and methods described herein, are a novel technique that generates active forces beyond the capacity of a passive mastopexy or reduction.

Since the laws of physics apply to biological systems as they do to any other system, the second law of thermodynamics describes the necessity of energy to maintain shape. The breast is a soft tissue open system that absorbs energy from earth's gravitational field resulting in ptosis or drooping, not chaos. Reshaping the ptotic breast with passive techniques is only a temporary solution, however, the pectoral major muscle can continuously provide the energy required. The present disclosure incorporates a new energy source to maintain a new soft tissue shape.

FIG. 1 shows a replica of a human body or the patient 10, including arms 12 and a torso 14, in which a breast insert or implant 16 (see FIG. 3) will be properly located and surgically implanted into the patient 10 for utilizing the apparatus, system and methods for the improved breast implant in the present disclosure.

Figure 2:
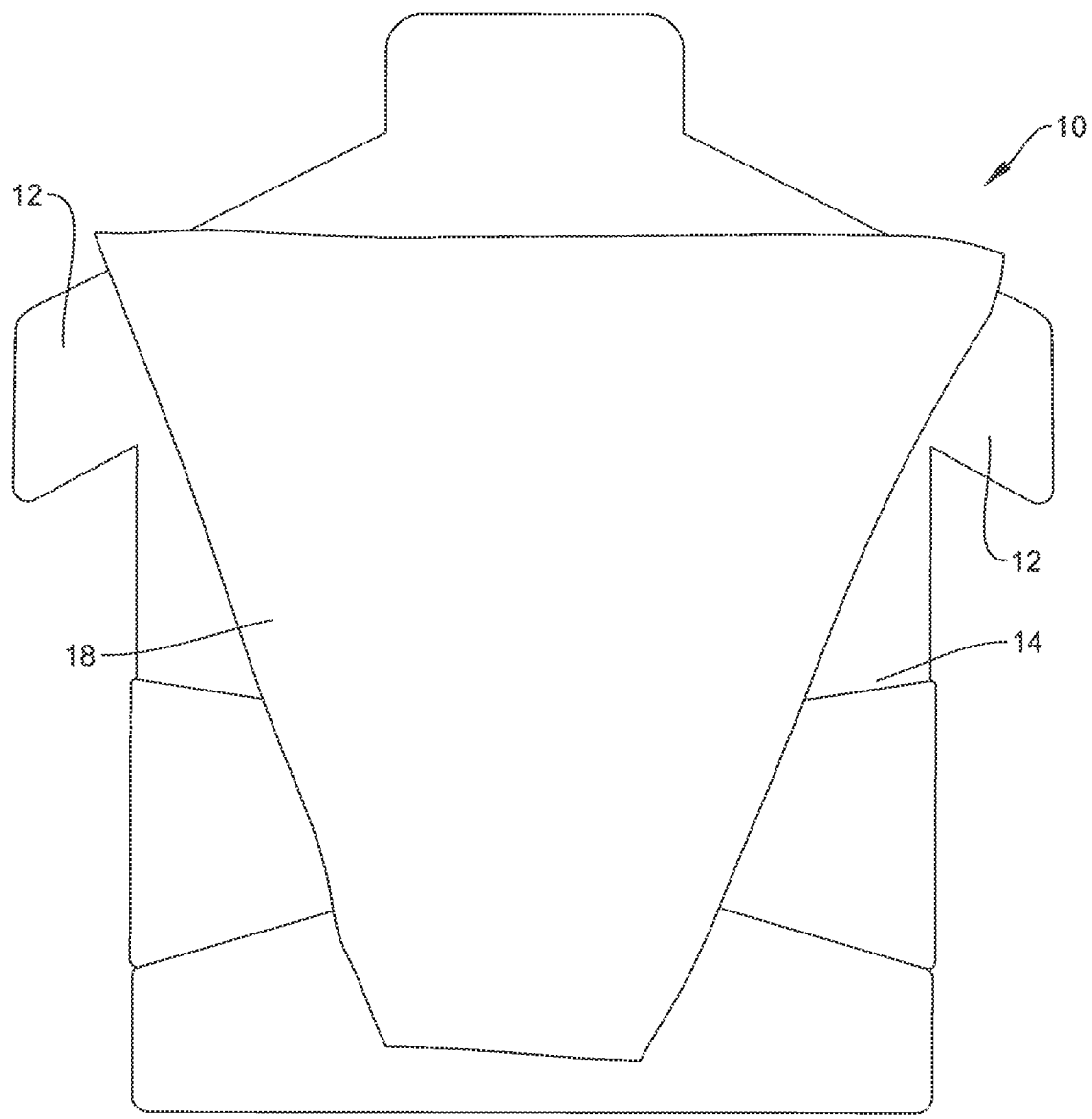
FIG. 2 illustrates an improved breast apparatus, system and method in accordance with one embodiment of the present disclosure.

FIG. 2 shows the same replica of the patient 10, including arms 12 and a torso 14, but also includes a replica of the patient's pectoralis major muscle 18, which will be used as the active force to generate lift of the breast or breast implanted insert 16, once the procedure has been completed. In an alternative embodiment, the insert 16 may be excluded and instead the breast itself will be used in conjunction with the breast implant device of the present disclosure for an improved breast surgery. In the discussion herein, the insert 16 will be referred to, however, it should be understood that wherever the insert 16 is referred to, the breast itself could be incorporated into the surgery, without the need for an insert 16. As such, the present disclosure can be an integrated breast implant device using the breast implant 16, the breast implant device 20 and the one or more straps 22 (see FIG. 6), or the breast implant device 20 can be separate parts, such that, as disclosed, the breast implant 16 is not necessarily needed, and the breast implant device 20 and straps 22 are either separate or combined (see FIGS. 6-8).

Figure 3:
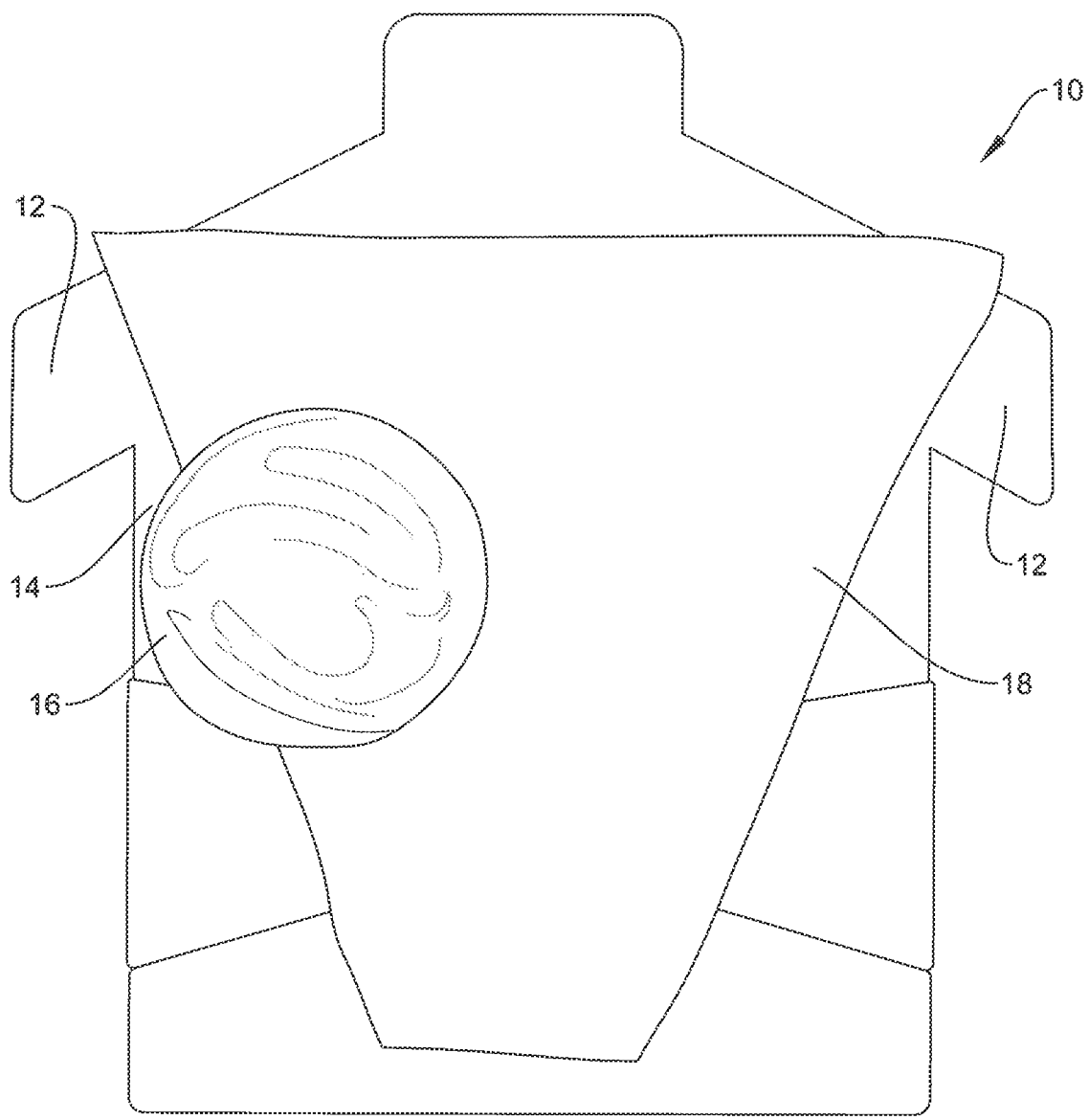
FIG. 3 illustrates an improved breast apparatus, system and method in accordance with one embodiment of the present disclosure.
Figure 4:
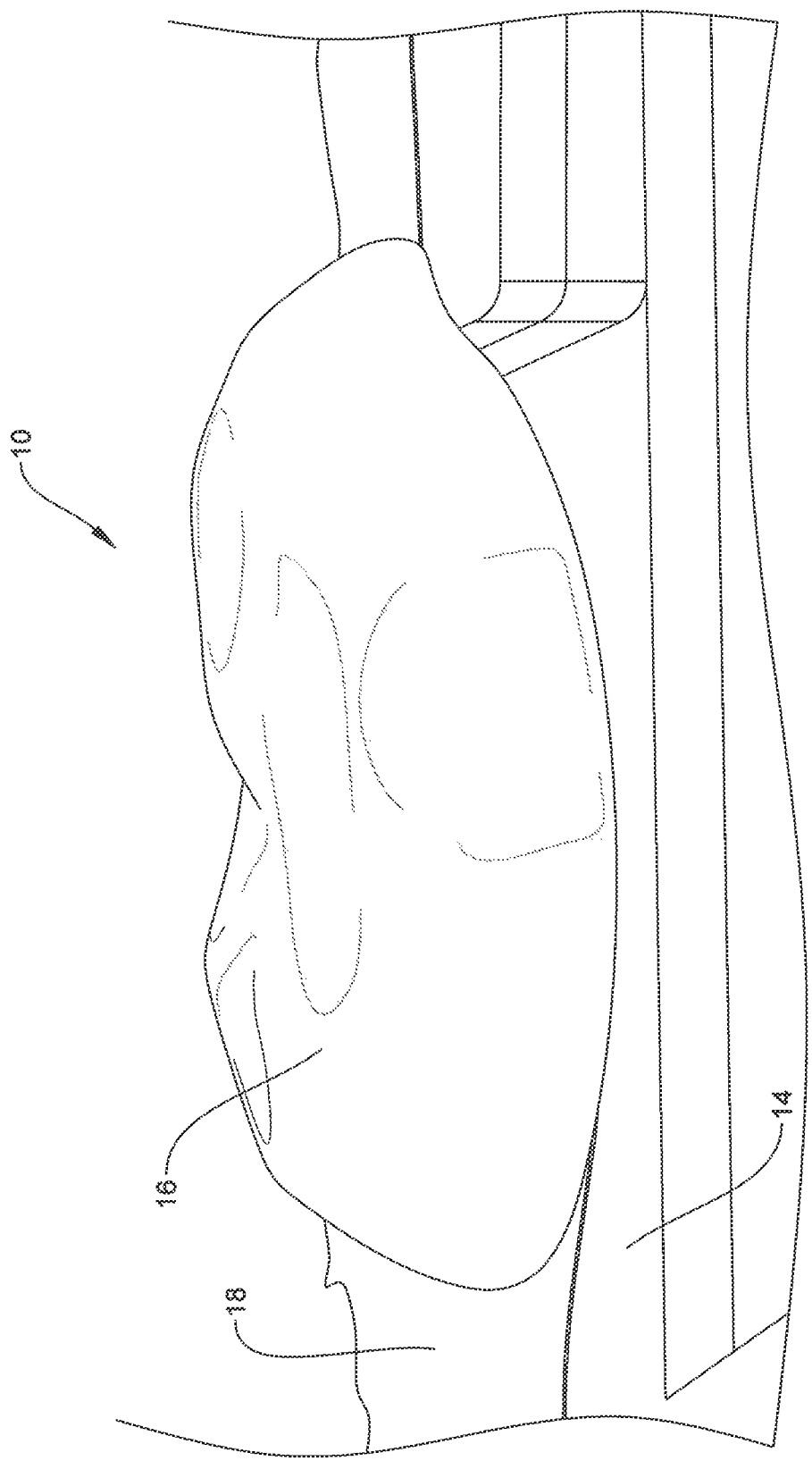
FIG. 4 illustrates an improved breast apparatus, system and method in accordance with one embodiment of the present disclosure.
Figure 5:
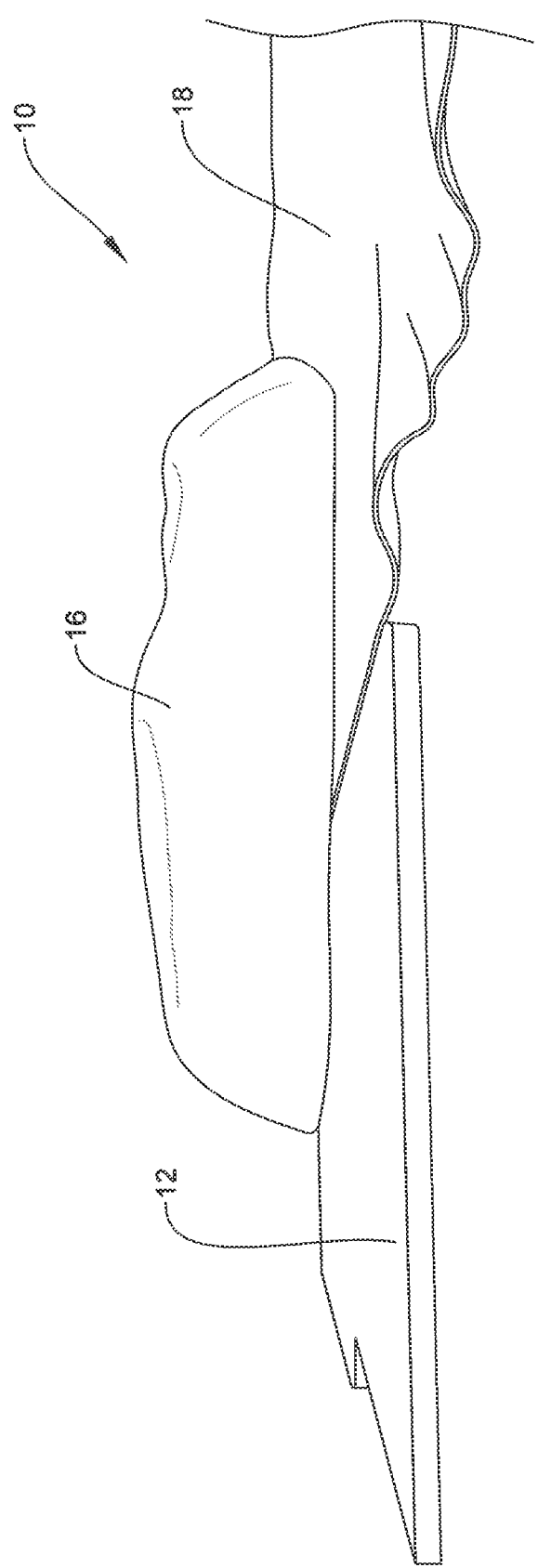
FIG. 5 illustrates an improved breast apparatus, system and method in accordance with one embodiment of the present disclosure.

FIGS. 3, 4 and 5 show the same replica of the patient 10, including arms 12 and torso 14, pectoralis major muscle 18, along with proper location or placement of the breast implant insert 16, from a top view (FIG. 3) and side views (FIGS. 4 and 5). The breast implant or insert 16 is placed in the approximate location once the procedure has been completed.

Figure 6:
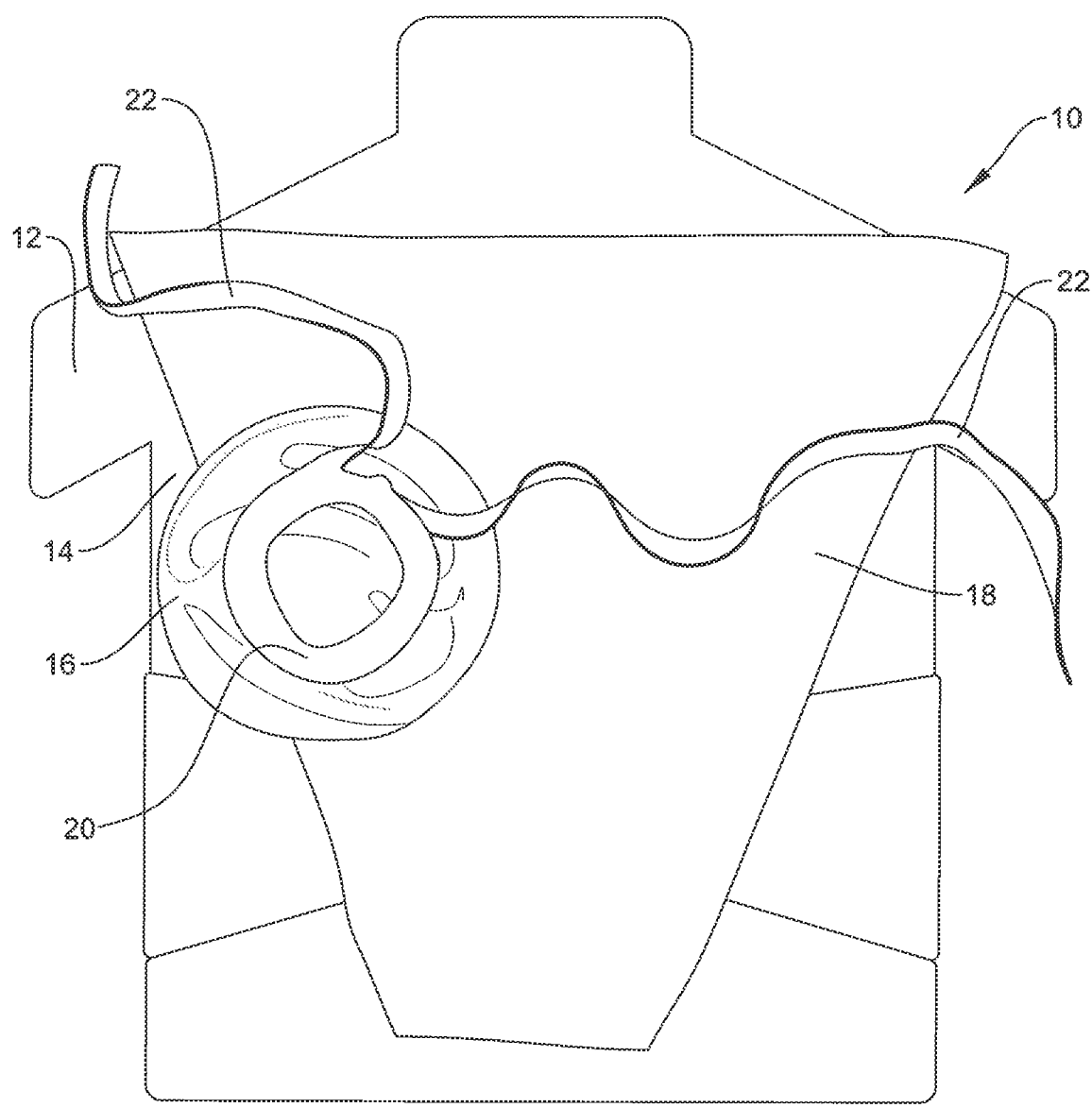
FIG. 6 illustrates an improved breast apparatus, system and method in accordance with one embodiment of the present disclosure.

FIG. 6 shows the replica of the patient 10 and insert 16 along with a separate device 20 and straps 22 for use in the improved breast implant in accordance with the present disclosure. As shown, the separate device 20 is ring shaped and incorporates one or more straps 22 to hold it in place in relation to the breast implant insert 16, as described in detail herein. The separate device 20 can be any configuration that, in combination with the straps 22, holds either the breast insert 16 or the breast itself in the proper location, and allows the muscle 18 to generate lift of the insert 16 or the actual breast (or the combination of both).

Figure 7:
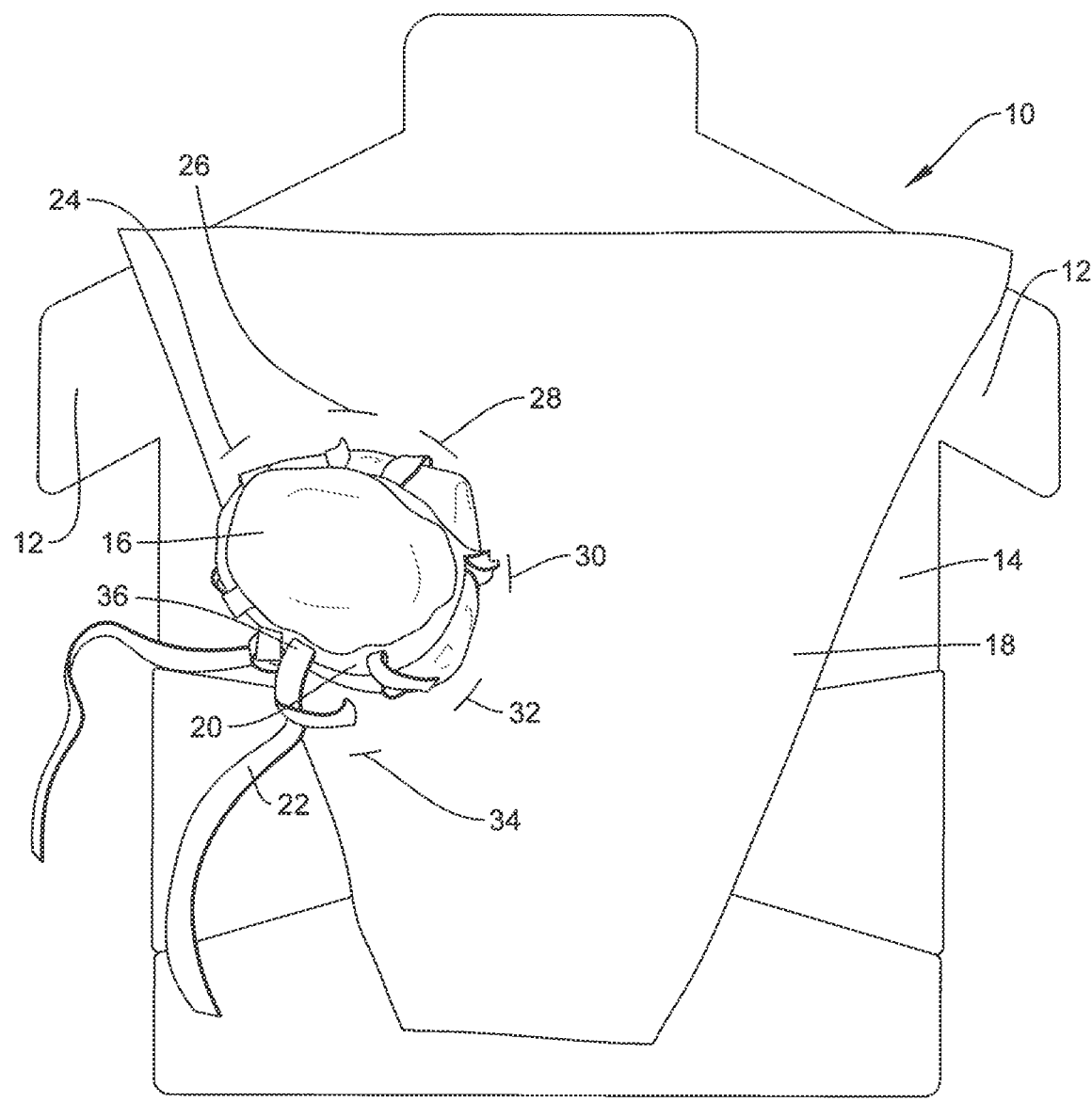
FIG. 7 illustrates an improved breast apparatus, system and method in accordance with one embodiment of the present disclosure.

FIG. 7 shows the replica of the patient 10 and insert 16 along with the separate device 20 and straps 22 for use in the improved breast implant in accordance with the present disclosure. As shown, the pectoralis major muscle 18 is dissected or cut in such a manner to allow the strap or straps 22 to be inserted into and through the pectoralis major muscle 18 at various locations 24, 26, 28, 30, 32, 34. As shown in FIG. 7, the strap 22 has been threaded through the pectoralis major muscle 18 at one location 34 and then threaded through a dissection or cut 36 in the breast implant device 20. This procedure is repeated by threading the one or more straps 22 through the dissections 24, 26, 28, 30, 32 in the pectoralis major muscle 18 and then through the dissections in the separate or breast implant device 20. The strap or straps 22 are then attached to themselves 22, to the breast implant 16 or to the separate device 20. There are many different ways to attach the straps, they can be sewn, stapled, tied, or connected in other known ways, and the scope of the present disclosure is not meant to be so limited.

Figure 8:
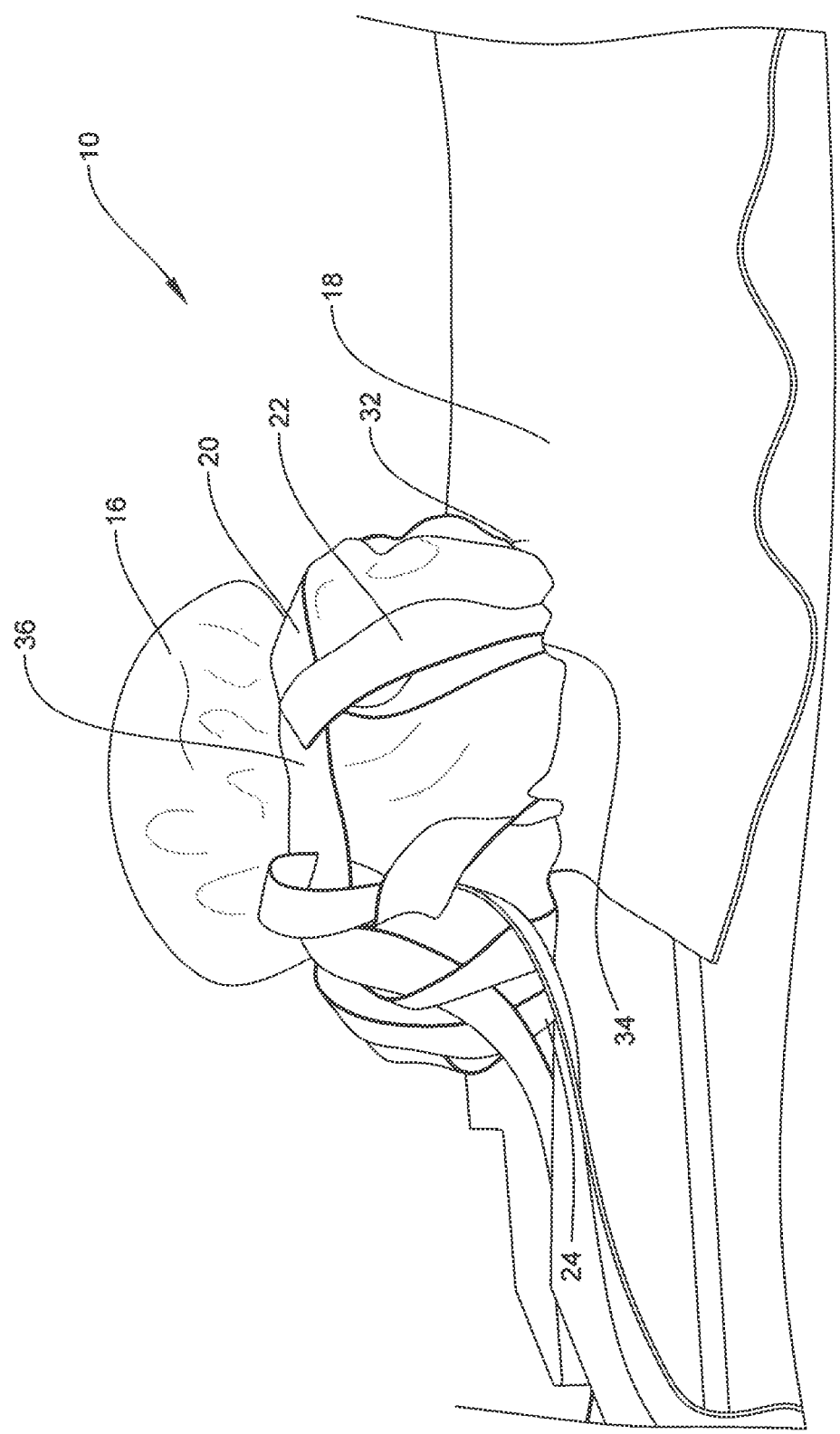
FIG. 8 illustrates an improved breast apparatus, system and method in accordance with one embodiment of the present disclosure.

FIG. 8 shows a side view of the replica of the patient 10 and insert 16 along with the separate device 20 and straps 22, once threaded through the pectoralis major muscle 18 at dissections 24, 32 and 34, for example, and the separate device 20 at dissection 36, for example. The strap or straps 22 are then attached to themselves, to the breast implant 16 or to the separate device 20, depending on the system or device being used, so that the muscle 18 can generate lift of the insert 16 or breast or both.

Figure 9:
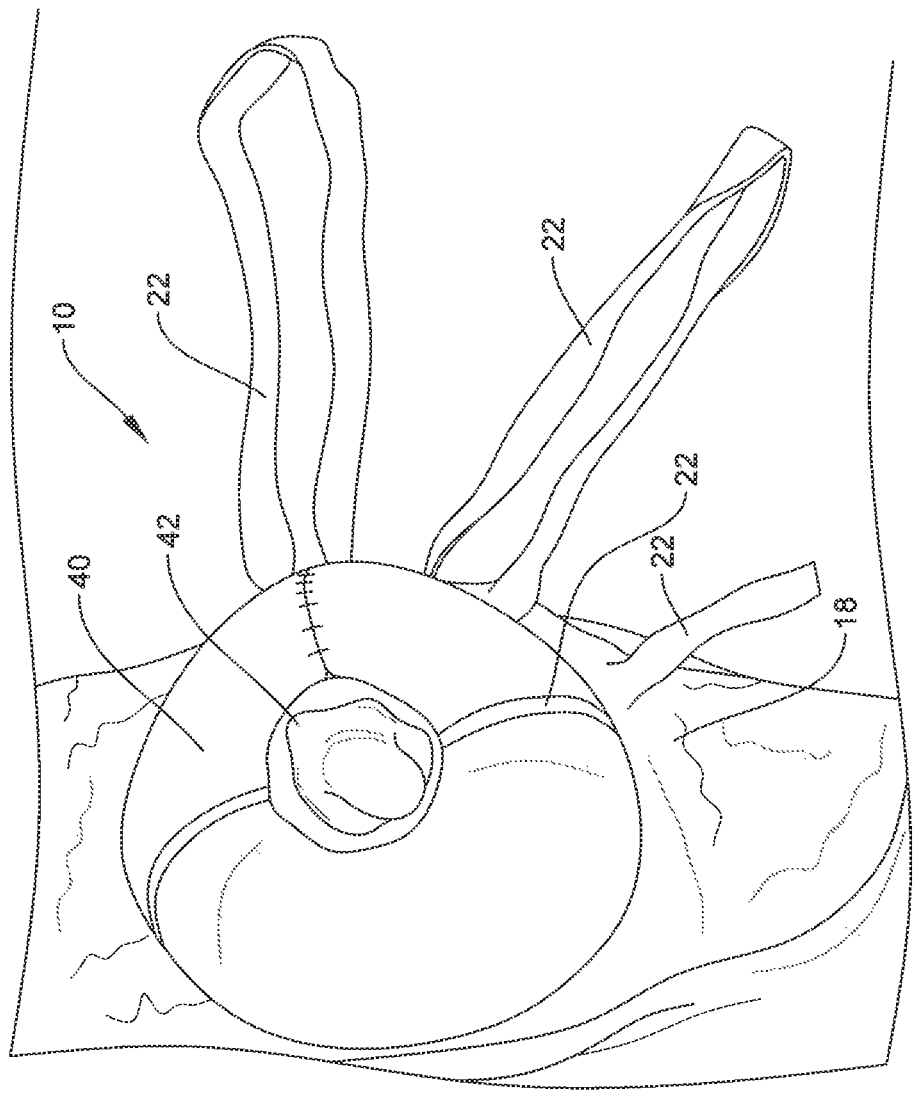
FIG. 9 illustrates an improved breast apparatus, system and method in accordance with one embodiment of the present disclosure.

FIGS. 9 (before) and 10 (after) show the preferred embodiment disclosed along with figures of the patient 10 using the actual breast 40 instead of an insert 16.

In the preferred embodiment, software analysis of chest images are combined with physical measurements and the woman's desires to generate a surgical blueprint. The blueprint provides origins, insertions and other parameters of the flaps and mound. These dimensions are marked on the patient in the standing and supine positions and are referred to throughout the operation.

Figure 10:
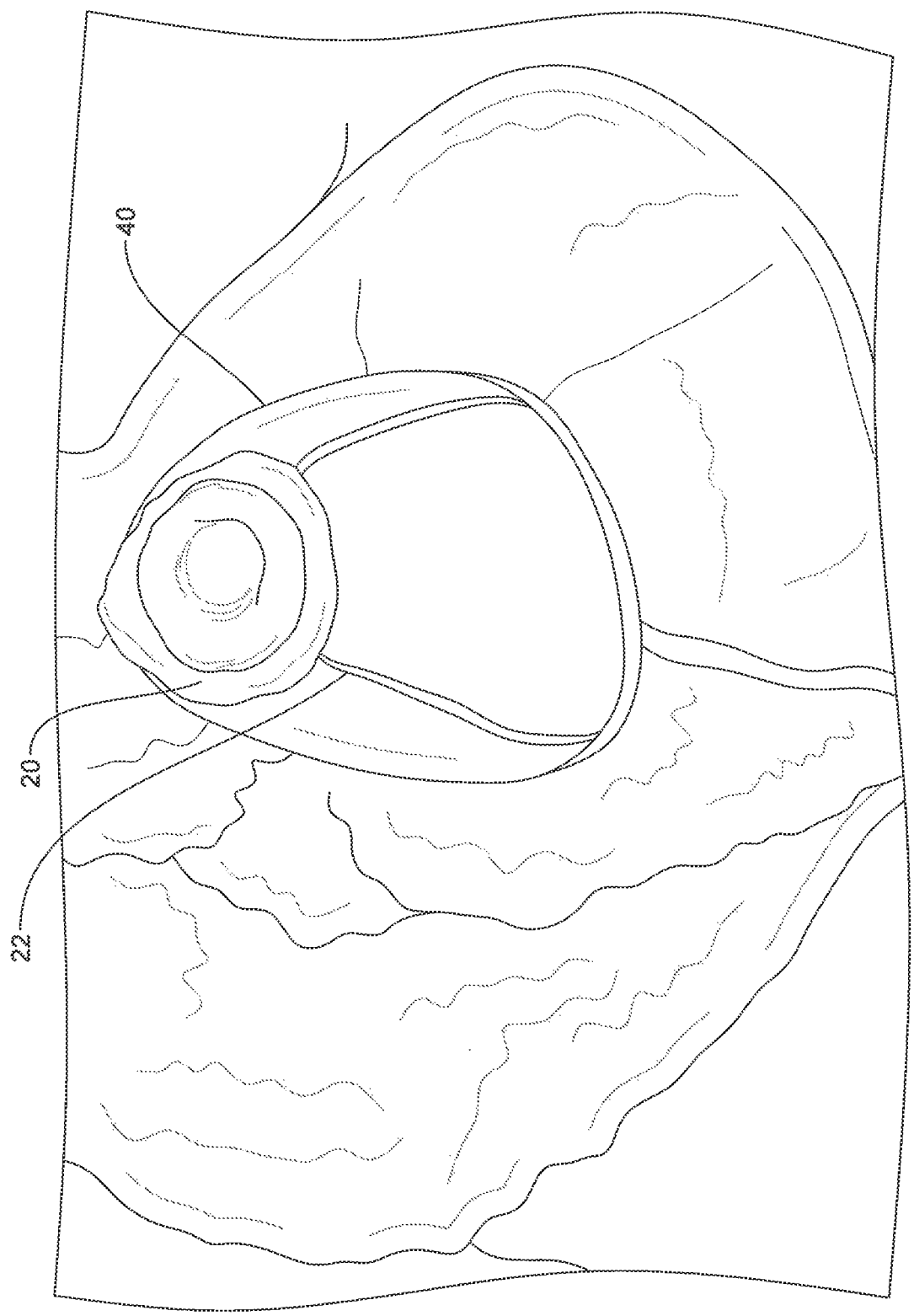
FIG. 10 illustrates an improved breast apparatus, system and method in accordance with one embodiment of the present disclosure.
Figure 11:
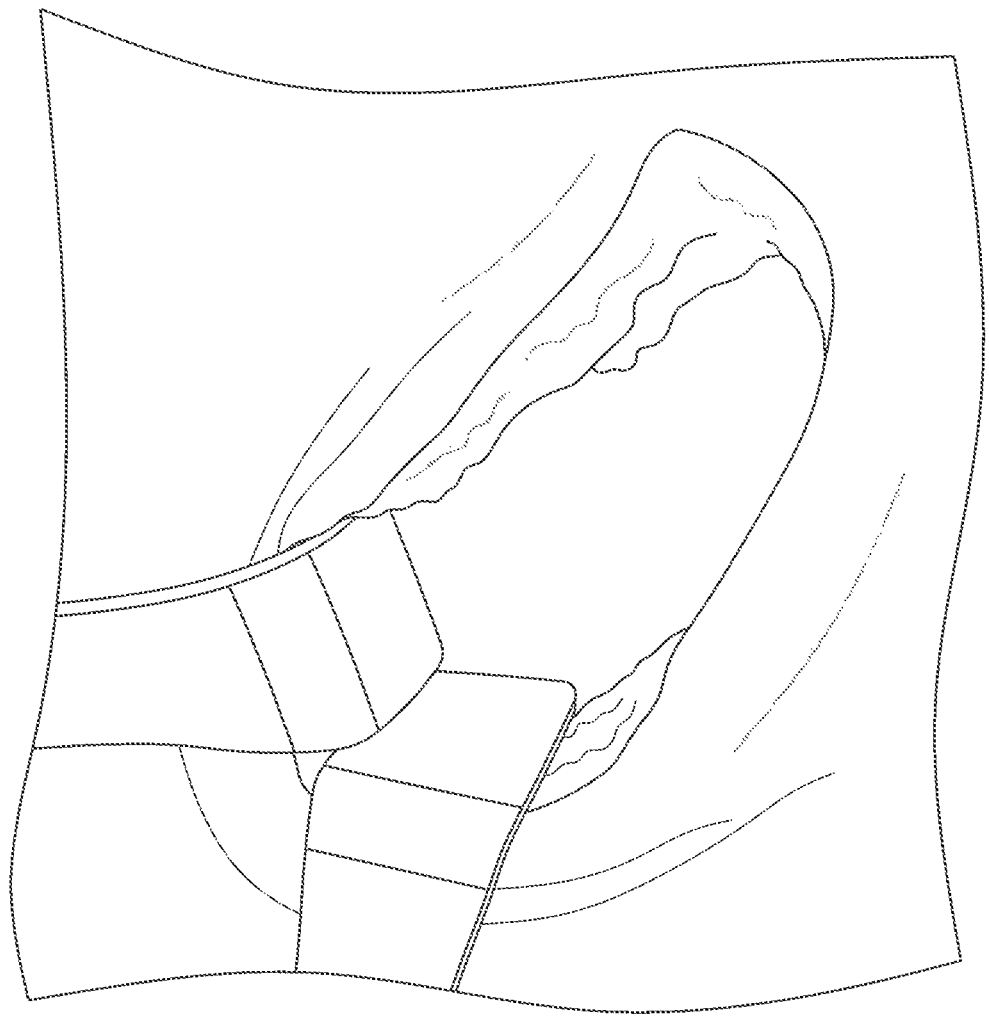
FIG. 11 illustrates an improved breast apparatus, system and method in accordance with one embodiment of the present disclosure.

FIGS. 9 through 12 show the breast implant method. In the operating room, an incision is made around the new areola (FIG. 11). Transverse incisions are made at the cephalad areola border and near the inframammary fold. The intervening skin is de-epithelized with a dermabrader or EPICUT®. The cephalad skin flap is elevated towards the clavicle, sternum and anterior axillary line at a depth and to a position determined by the blueprint. The retropectoral space is entered near the axilla, and dissected leaving the pectoral major muscle origins attached. If the woman desires volume reduction, then breast tissue is removed inferior-laterally.

In certain situations, artificial skin, such as synthetic material or biological material can be used with or instead of the patient's skin. In these situations, by using synthetic material, the resulting breast may be an improvement over the resulting breast if the synthetic material were not available or used in the surgery.

In the preferred embodiment, FIG. 9 shows the de-epithelized skin, which is then rotated into a cone 42 and three straps 22 are elevated from the base of the cone at the 12 o'clock, 1:30, and 3 o'clock positions in the right breast 40. The 3 o'clock strap 22 is sutured to the muscle and fascia overlying the sternum. This passive strap transposes the cone 42 cephalad-medial, rotates the cone 42, sets cleavage and stabilizes the cone 42 while the other straps 22 are placed. The 12 o'clock and 1:30 straps 22 are passed through breast tissue lying outside the cone 42 entraining it, then looped through the pectoral major muscle 18 back to the base of the cone 42. This is done repeatedly and the resulting attachments to the base of the cone 42 create dermal loops, which contain pectoral major muscles 18 loops that are designed to generate active cephalad-medial force vectors.

FIG. 10 shows the breast after all three straps 22 are placed. The tension is adjusted to ensure that the cone 42 is within the horizontal and vertical grids determined by the alignment points from the blue print. The angle of inclination of the cone 42 is adjusted to create slight cephalad and lateral tilt. The skin flap is transposed over the cone 42 and the wound is temporarily stapled closed.

Figure 12:
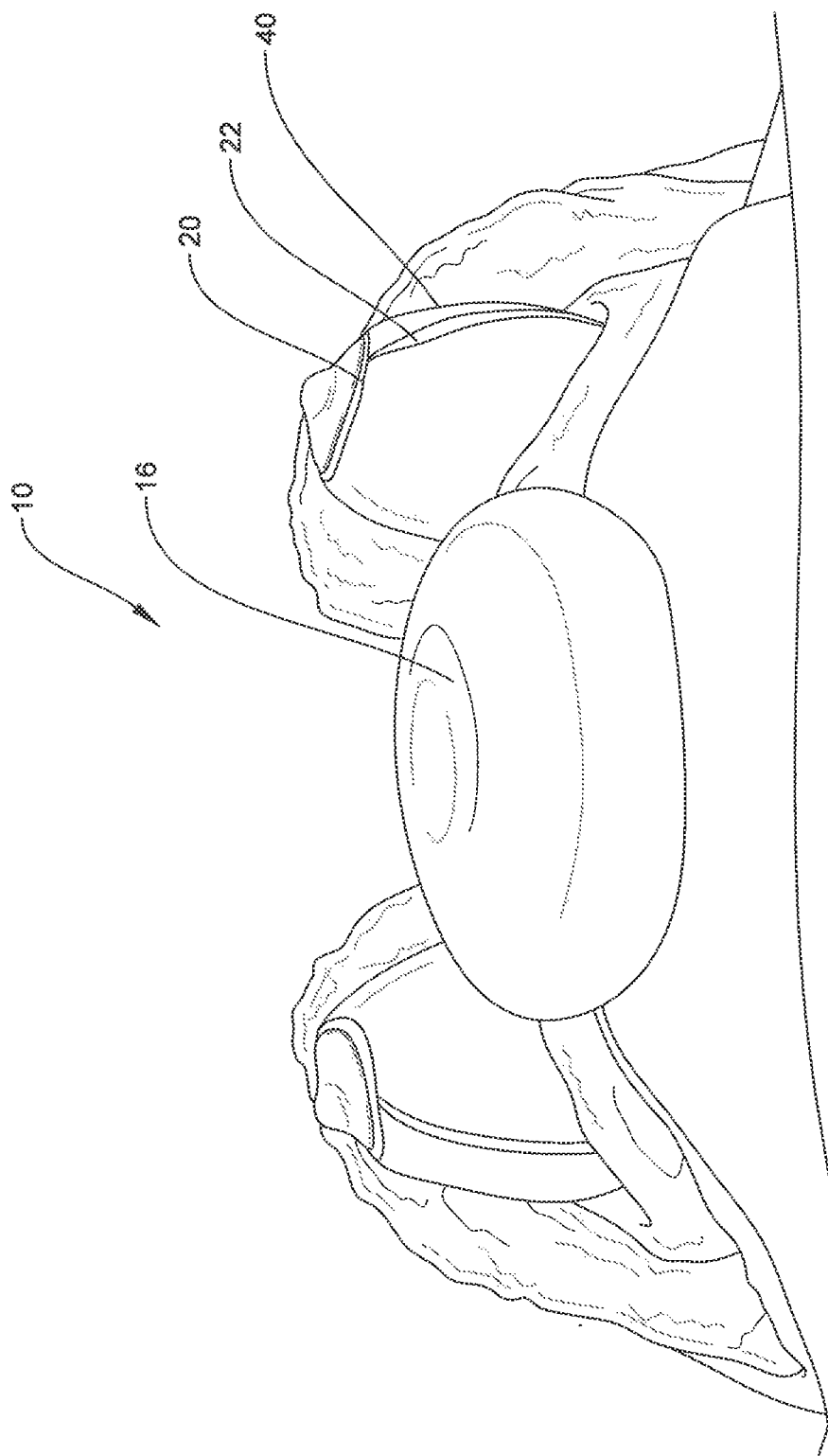
FIG. 12 illustrates an improved breast apparatus, system and method in accordance with one embodiment of the present disclosure.

Next, the patient 10 is elevated vertically and the position, shape and contour irregularities are determined. The patient 10 returns to the supine position, the staples removed and corrections made. The opposite breast 40 is done in a mirror image manner. Upon completion of both breasts 40, they are re-examined for symmetry. Corrections are made, drains placed, and the wounds irrigated with antibiotic solution. The incisions are closed in layers, the patient 10 is elevated vertically and the site for the nipple areola complex is marked. FIG. 12 shows the patient after returning to the supine position, the tissue is excised and the nipple areola complex is delivered and closed in layers. The dressing consists of steri-strips, fiberglass moulage, fluffs and ace wraps.

In a previous study, sixty-five women underwent no vertical scar breast weight transfer. This technique was universally applied to all women who desired mastopexies or reductions. No women were offered other techniques preoperatively or switched intraoperatively. Implants or fat transfers were not required. Women with previous breast augmentation, mastopexy or reduction are not included in these particular study results, although these women may be included in the study technique. Ages ranged from 17 to 68 with the mean age of 40. Body mass index ranged from 20.3 to 35.5 with a mean of 26.4. The weight was normal in 28%, 64% were overweight and 8% were obese.

Follow up questionnaires were obtained from 36 women (55%). Duration of follow-up ranged from 10 to 23 months with a mean of 15 months. None of the women became pregnant during the follow up. When asked why they chose this technique, 89% stated "no vertical scar". The areola scar was excellent in 32%, good in 44%, fair in 15%, and poor in 9%. The transverse scar was excellent in 20%, good in 34%, fair in 28% and poor in 18%. The position of the transverse scar was satisfactory in 79% and unsatisfactory in 21%. The position of the breast was as desired in 92%, too low in 5% and one woman (3%) "a little too high". Anterior breast projection was adequate in 86% and inadequate in 14%. Upper pole fullness was increased in 86%, and unchanged in 14%. The breast shape was as desired in 89% and undesirable in 11%. Nipple sensation was increased in 37%, was unchanged in 44%, was decreased in 17% and 5% had complete numbness. One woman had bilateral nipple numbness and two women had left nipple numbness.

Weight removal was less than 300 grams in 70%, 300 to 500 grams in 23% and more than 500 grams in 7%. Twenty-six women (74%) had neck, shoulder or back pain attributed to the breast pre-operatively. Of these, 54% had complete relief of pain, 38% had decreased pain and two women (8%) have the same pain. In one woman the pain was relieved completely after surgery, but returned. She had a resection of 250 grams from the right, 270 grams from the left and was reduced from a 36DD to a 36D. The second woman had a resection of 131 grams from the right, 271 grams from the left and was reduced from a 36DD to a 36C. Women reported improved posture in 91% and no change in 9%.

The most frequent complications were dog-ears, which occurred in 60%. Of these, 60% underwent revision under local anesthesia in the office at no cost. Periareolar infection occurred in one woman (3%) and fat necrosis occurred in another (3%). Both women required incision and drainage under local. One woman, a 34D, requested fat transfer 16 months post-surgery at the time of elective abdominoplasty for massive weight loss. Overall results were excellent in 50%, good in 36% and fair in 14%.

Aesthetics and function are critical factors influencing a women's decision to undergo surgery and the technique selected. Although many women are functionally impaired by their breasts, the vertical scar of the traditional techniques is unacceptable to many. Aesthetics dominated with 89% selecting no vertical scar as the motivating factor despite the fact that 74% had pain. Women in the childbearing years endure dysfunctional breasts because of the known complications with breast feeding, sensation and to avoid vertical scars. In this review, none of the women became pregnant during the follow up. However, post-operative women have successfully breast-fed. Since the nipple is not pedicle based and the major lactiferous ducts are not injured, the ability to breast feed is maintained.

Women who have completed child bearing or do not desire pregnancy often request mastopexy or reduction. They are frequently offered breast implants as an adjuvant or alternative. Implants are used to create upper pole fullness, refill deflated breasts or to "lift" the breast without the unacceptable scars. The laws of physics also apply to implants. In the pre-pectoral position, passive forces resist implant descent and shape change from the force of gravity. Implant manufacturers have recognized these complications and developed textured implants to resist descent and increased cohesiveness to resist deformation.

In the retro-pectoral position, the implant is exposed to the same forces as a pre-pectoral implant with the additional active force created by the pectoral major muscle. Partial pectoral major muscle detachment is used to decrease implant displacement and deformation but irreversibly damages the muscle. Implants in the partial retro-pectoral position are displaced inferior-laterally by active pectoral major muscle forces. Manufacturers have recognized this complication and developed new materials for implantpexy. These materials are attached to the mobile inferior-lateral edge of the stretched pectoral major muscle and the fascia overlying the chest. Implantpexies are similar to mastopexies and are limited by the material providing the support and their points of attachment. Dynamic forces can exceed the mechanical strength at the points of attachment, resulting in failure and implant descent.

In the totally retro-pectoral position, active force generated by the inferior-lateral edge of the non-stretched pectoral major muscle generates cephalad-medial force on the implant, which is greater than gravity. The implant is mechanically stable but the overlying breast tissue is not lifted. Passive mastopexy and reduction techniques do not produce active cephalad-medial breast force vectors. As a result, if a total retro-pectoral implant is placed with a passive mastopexy or reduction, the implant maintains stable position but the breast tissue descends creating misalignment. However, if breast weight transfer is combined with a total retro-pectoral implant, the pectoral major muscle provides active lift to both the implant and the breast tissue. Deferential descent does not occur and the misalignment is avoided.

Implants are required for mastopexies or reductions using the plus minus technique. Excess inferior breast tissue is resected and implant volume is added superiorly. Women who desire mastopexy often state, "I don't want my breast bigger or smaller, but back where they used to be." The breast volume is adequate and implants are not required. Women who need reductions by definition have excess breast volume and implants are not required. If superior volume is needed, rotation and transposition of living tissue is biomechanically preferable to adding the dead weight of an implant. Removal of normal breast tissue and replacing it with synthetic material violates fundamental plastic surgical principals. For these reasons, the plus minus technique is not recommended.

Implants alone have been used as an alternative to mastopexy. Since implants cannot lift breast tissue, the inframammary fold is often lowered to align the nipple to center of mass of the implanted breast. Women prefer breast and inframammary fold elevation to create a youthful, perky, sexy appearance as opposed to the descended breast that appears heavy and matronly. Adding the mass of an implant into a breast that fails to maintain position or shape due to gravity is contraindicated, unless a new active opposing force is created. Because of these and all the other known implant complications, they are best avoided.

Multiple techniques for mastopexy or reductions have been described but none is universal. An alternative to empirical techniques is to approach breast surgery as an engineering problem that requires an individualized solution. Software analysis of the chest images, physical measurements and the woman's desires are combined to derive the optimal solution mathematically. This technique is universally applicable and generates individualized solutions that maximize results. Computer aided design is an established engineering technique that is applicable to breast surgery.

The breast 40 is engineered to change position, shape, and feel. Rigid materials are not permitted in a soft organ. The only tissues available are muscle, fascia, fat, parenchyma and skin. Of these, parenchyma is the best tissue to resist compression and generate anterior projection. Unfortunately, women in need of surgery frequently are overweight or obese and little parenchyma is available. Vertical "pillars" made from soft tissue lack the mechanical strength to increase projection.

An alternate technique uses de-epithelized skin to construct the internal cone 42, which encloses fat and parenchyma in a semi-closed space. The cone 42 can be modified to produce round or anatomical shapes and the desired projection. The dermal straps 22 function and appear like tendons, as shown in FIG. 11, transferring muscle 18 force to oppose gravity. The pectoralis major muscle 18 compresses the cone 42 to increase projection, increases the breast 40 firmness, maintains the elevated position and provides the energy required to maintain the new shape. Dynamic forces stretch the pectoral major muscle 18, which absorbs kinetic energy without mechanical failure and the breast 40 returns to the original position without over correction. These biomechanical properties are superior to passive surgical techniques and implants, as shown in FIG. 12.

The transverse incisions are the greatest source of patient dissatisfaction. Dog-ears (not shown) and incisions significantly above the inframammary fold are undesirable. The techniques has been modified to now use sutures to pull the medial dog-ear laterally and the lateral dog-ear medially. This displaces the excess skin toward the midline of the incision and the horizontal excess is redistributed by the vertical meridian tension.

Malposition of the transverse incision occurs when the vertical descent of the nipple areola complex is not long enough to reach the new inframammary fold. This is predicted pre-operatively and the alternatives are offered. The woman's choices are, decreasing the breast volume, decreasing the anterior projection, elevating the new inframammary fold higher or accepting the incision above the inframammary fold, with revision at six months. The techniques has also been modified to suture scarpa's fascia to the rib periosteum at the vertical meridian of the incision. The posterior attachment minimizes incision translocation onto the breast mound.

The oncologic implications of a new surgical technique must be considered. Neither breast implants nor foreign materials are required. Breast imaging and physical examination are not compromised. Only dermis is placed retropectoral, which does not potentiate breast cancer. Further, the no vertical scar breast weight transfer technique can be used for mastectomy, reconstruction and the opposite breast surgery. Symmetry is achieved by using the same external skin dimensions for both the mastectomy and opposite breast. The mastectomy is performed through the cephalad transverse incision. The de-epithelized dermis can be harvested as an autogenous graft to cover the implant reconstruction. Implant reconstruction frequently results in a high hemispherical breast, which can be matched using the no vertical scar breast weight transfer technique. Women are more likely to accept surgery on the noncancerous breast if they can avoid the vertical scars and loss of nipple sensation.

In summary, women do not want vertical scars on their breasts. Breast weight transfer relieves pain. Also, implants are undesirable and not required. Combining mathematics, physics and engineering with anatomy, physiology and plastic surgery principals creates beautiful, functional breasts. No vertical scar breast weight transfer is a new universal technique that satisfies women's esthetic and functional desires.

Additionally, in the preferred embodiment, the surgery described herein, including the system and method in which one or more straps are looped through a muscle then back repeatedly, and eventually attached to themselves (or to other parts of the system), can be utilized in other places in the body. In doing so, when a patient changes position, the gravitational force that is generated by will pull on the straps, which will then pull on the particular muscle and thereby stimulates the muscle to respond.

It will be understood that the embodiments of the present disclosure, which have been described, are illustrative of some of the applications of the principles of the present disclosure. Although numerous embodiments of this disclosure have been described above with a certain degree of particularity, those skilled in the art could make numerous alterations to the disclosed embodiments without departing from the spirit or scope of this disclosure.

All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosed system and methods.

Additionally, joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosed apparatus, system and methods as disclosed herein.

What is claimed is:

1. An improved breast implant device to be implanted in a user in which a user's pectoralis major muscle is used to generate active lift, comprising:
    a breast implant device, said breast implant device comprising one or more straps;
    said one or more straps of a first length to be looped into and through one or more differently located dissections in said user's pectoralis major muscle and further of a second length to be returned to the breast implant device;
    said user's pectoralis major muscle comprising one or more neuromuscular spindles, said one or more straps further configured to be connected to themselves after being looped into and through said user's pectoralis major muscle in said differently located dissections;
    wherein when said pectoralis major muscle senses a change in user's position from supine to vertical, the gravitational force pulls on the one or more straps, thereby pulling on said pectoralis major muscle, stimulating said one or more neuromuscular spindles, thereby generating active lift on the breast implant device.

2. The improved breast implant device of claim 1, in which said breast implant device is integrated with a breast implant and said one or more straps.

3. The improved breast implant device of claim 1, in which said breast implant device is separate from said breast implant whereby said breast implant device comprises said one or more straps.

4. The improved breast implant device of claim 1, in which said breast implant device, said breast implant and said one or more straps are all separate from each other prior to being connected.

5. The improved breast implant device of claim 1, in which said straps of said implant device are looped together after being looped through said user's pectoralis major muscle.

6. The improved breast implant device of claim 1, in which said straps of said implant device are looped back to said breast implant device after being looped through said user's pectoralis major muscle.

7. The improved breast implant device of claim 1, in which said straps of said implant device are connected together after being looped through said user's pectoralis major muscle.

8. The improved breast implant device of claim 7, in which said straps of said implant device are sewn together after being looped through said user's pectoralis major muscle.

* * * * *